United States Patent
Benoit et al.

(10) Patent No.: US 6,183,783 B1
(45) Date of Patent: Feb. 6, 2001

(54) METHOD FOR PREPARING MICROCAPSULES COMPRISING ACTIVE MATERIALS COATED WITH A POLYMER AND NOVEL MICROCAPSULES IN PARTICULAR OBTAINED ACCORDING TO THE METHOD

(75) Inventors: Jean-Pierre Benoit, Avrille; Joël Richard, Longue, both of (FR); Curt Thies, Ballwin, MO (US)

(73) Assignee: Mainlab, Angers (FR)

( * ) Notice: Under 35 U.S.C. 154(b), the term of this patent shall be extended for 0 days.

(21) Appl. No.: 09/269,173

(22) PCT Filed: Sep. 24, 1997

(86) PCT No.: PCT/FR97/01674

§ 371 Date: Jun. 22, 1999

§ 102(e) Date: Jun. 22, 1999

(87) PCT Pub. No.: WO98/13136

PCT Pub. Date: Apr. 2, 1998

(30) Foreign Application Priority Data

Sep. 25, 1996 (FR) .................................................. 96 11665

(51) Int. Cl.⁷ .................................. A61K 9/16; A61K 9/32
(52) U.S. Cl. .......................... 424/497; 424/490; 424/401; 424/59
(58) Field of Search .................................. 424/490, 497, 424/401, 439, 59

(56) References Cited

U.S. PATENT DOCUMENTS

| | | | | |
|---|---|---|---|---|
| 5,043,280 | * | 8/1991 | Fischer et al. ................... | 435/235.1 |
| 5,424,076 | | 6/1995 | Gorissen et al. .................. | 424/501 |
| 5,501,863 | * | 3/1996 | Rossling et al. .................. | 424/489 |
| 5,667,806 | * | 9/1997 | Kantor ................................ | 424/484 |
| 5,766,637 | * | 6/1998 | Shine et al. ....................... | 424/497 |

FOREIGN PATENT DOCUMENTS

| | | |
|---|---|---|
| 0 542 314 | 5/1993 | (EP) . |
| 0 706 821 | 4/1996 | (EP) . |
| WO92/11000 | 7/1992 | (WO) . |

* cited by examiner

Primary Examiner—Thurman K. Page
Assistant Examiner—P. E. McQueeney
(74) Attorney, Agent, or Firm—Jacobson, Price, Holman & Spern, PLLC

(57) ABSTRACT

The invention concerns a method for preparing microcapsules containing an active substance coated with a substantially polar polymer film, characterized in that it consists in the following steps: suspending an active substance insoluble in a substantially polar polymer solution in an organic solvent, said substantially polar polymer being insoluble in liquid or supercritical $CO^2$, said organic solvent being soluble in liquid or supercritical $CO^2$; contacting the suspension with liquid or supercritical $CO^2$ so as to extract the solvent from the polymer in a controlled manner and ensure the coacervation of the polymer; substantially extracting the solvent by means of supercritical $CO^2$ and draining off the $CO^2$/solvent mixture; recuperating the microcapsules in the form of dry powder. The invention also concerns microcapsules containing an active substance coated with a substantially polar polymer selected among the group consisting of polysaccharides, cellulose derivatives, acrylic, methacrylic polymers or derivatives of esters of vinyl, polyesters, polyamides, polyanhydrides, polyorthoesters and polyphosphazenes, characterized in that the polymer film has low surface energy and is free from organic solvent and in that the microcapsules are obtainable by said method.

20 Claims, 1 Drawing Sheet

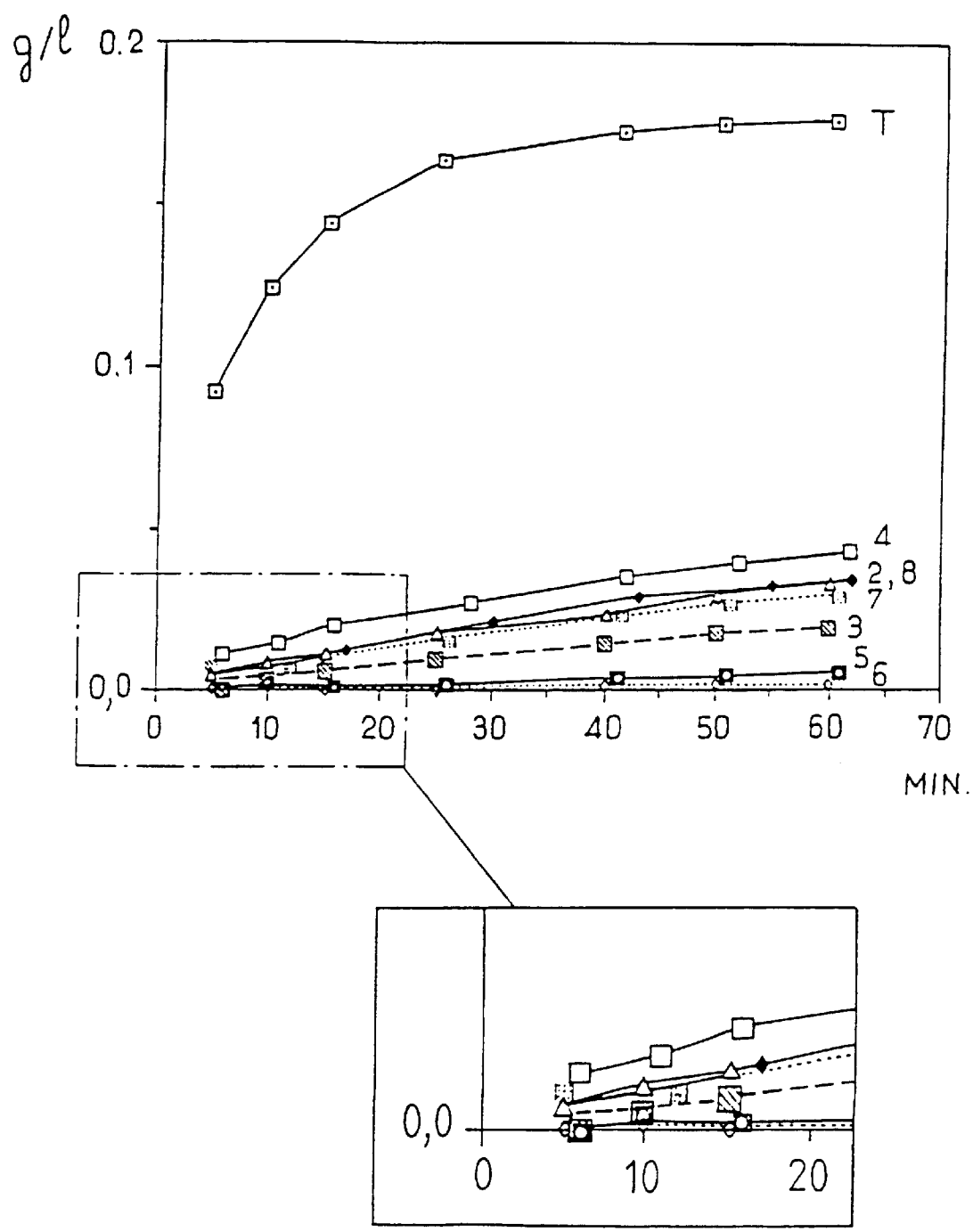

METHOD FOR PREPARING MICROCAPSULES COMPRISING ACTIVE MATERIALS COATED WITH A POLYMER AND NOVEL MICROCAPSULES IN PARTICULAR OBTAINED ACCORDING TO THE METHOD

The invention relates to the field of the microencapsulation of active substances. It relates to a process for preparing microcapsules of the type comprising an active substance coated with a layer of polymer by the so-called supercritical fluid technique.

It also relates to novel microcapsules comprising in particular pharmaceutical or cosmetic substances or processed foodstuffs.

A great many documents describe the principles and the methods for preparing such microcapsules, for example J. A. Bakan, Microencapsulation via Coacervation—Phase Separation, National Industrial Research Conference, Land O'lakes, Wis., June 1966. Other publications are cited in the article by J. P. Benoit et al., Microencapsulation Methods and Industrial Applications, Marcel Dekker, Inc. 1996, pages 35–72.

The size of the microcapsules obtained is of the order of 0.5 to 200 μm (sometimes more). They are composed of a nucleus of active material covered with a coating agent.

The coating agent is chosen from a range of various compounds (hydrocolloids, hydrophobic polymers, waxes, fats or enteric agents, and the like) according to various factors:

the goals targeted by the microencapsulation: for example, to mask the taste or the smell of the active principle per os, to decrease the volatility of certain liquids, to increase the physicochemical stability of the active principle, to prevent the coalescence of the droplets within an emulsion, to modify and improve the compression of the active principle, to delay or prolong the action of a medicament, to have an enteric-coated pharmaceutical dosage form, and the like, the desired method of release of the active principle (dissolution, diffusion, and the like), the physicochemical nature of the nucleus (size, compatibility, and the like), the microencapsulation methods (fluidization, turbine, desiccation by nebulization, interfacial polymerization, coacervation, and the like).

The preparation of microcapsules is commonly carried out by the so-called coacervation method, which will be briefly restated below:

Chemical or physicochemical modification of a medium comprising an active substance in suspension in a solution of polymer in a solvent causes the coacervation (or aggregation) of the polymer.

The coacervate droplets thus formed are adsorbed at the surface of the particles of active material and form a continuous coating.

The medium is subsequently subjected to complete desolvation and optionally to crosslinking of the polymeric chains, which results in the production of microcapsules.

All these abovementioned methods very often require toxic and polluting organic solvents with a relatively high industrial cost.

For this reason, the Applicant Company has for several years attempted to search for alternative methods which make it possible to prepare microcapsules without the aid of organic solvents or at least without chlorinated solvents (dichloromethane, chloroform, and the like).

Thus it is that the Applicant Company has recently provided, by Patent Application EP-A-706,821, the use of the properties of $CO_2$ in the supercritical (SC) state as solvent.

$CO_2$ is said to be in the supercritical state (SC $CO_2$) if the temperature is greater than 31° C. and its pressure is greater than $73.8 \times 10^5$ Pa.

This is because the latter simultaneously retains the properties of a gas, such as its high diffusion, and acquires those of a liquid, such as its relative density, which is 0.7 kg/cm$^3$ at the supercritical point. $CO_2$ in this state has a significant solvating power. It is said to be similar to heptane.

The advantages of SC $CO_2$ are therefore:

a high solvating power for fairly low temperature conditions (30° C.), which is not without advantage in the case of the use of thermolabile active principles;

a high variation in this solvating power for low variations in pressure, its non-toxic nature, the ready separation of the solvent-solute mixture by simple decompression;

its low cost in comparison with the current organic solvents.

The method according to the abovementioned patent application involves suspending, in an autoclave, an active substance which is insoluble in supercritical $CO_2$ and then introducing the coating agent into the autoclave, which coating agent is found in the solute state in supercritical $CO_2$. The pressure and/or the temperature are subsequently modified, so that the solubility of the coating agent in $CO_{O2}$ decreases. The affinity of the coating agent for the surface of the active substance increases, for this reason causing the adsorption of the coating agent around the particles of active substance. Once deposition is accomplished, the autoclave is depressurized and the microcapsules are recovered. This method gives excellent results for coating agents which exhibit a good solubility in $CO_2$, that is to say for coating agents which have a marked lipophilic nature and low molar masses, such as fatty substances (waxes, fatty alcohol triglycerides, fatty acids) and many other compounds.

However, in the case of polymers which exhibit a substantially more polar nature than fatty substances and a higher molar mass (acrylic polymers, vinyl polymers, polysaccharides), this method is not very satisfactory.

This is because these polymers are not soluble in supercritical $CO_2$. Now this is an essential condition in order to be a coating agent according to the method disclosed in Patent Application EP-A-706,821. The use was indeed envisaged, in this patent application, of a low level (<5%) of an entraining agent, such as ketones, alcohols, esters and chlorinated solvents, as a mixture with $CO_2$ with the aim of increasing the solubility of the polymer in the supercritical phase. However, such an alternative form would nevertheless result, in many cases, in a low degree of solubilization of the polymer with a substantially polar nature and in a significant modification of the supercritical conditions, or in a disappearance of the supercritical phase, replaced by a two-phase system.

Furthermore, mention is made of the document U.S. Pat. No. 5,424,076, which discloses a method based on an atomization or spray-drying technique in the presence of supercritical fluid.

Firstly, although the document mentions the fact that the active substance is in dispersed form, all the examples relate to solutions of these active materials. Furthermore, this method results in the production of microspheres and not of microcapsules. The fundamental difference between microspheres and microparticles should be remembered. Microspheres are matrix systems in which the active material is homogeneously dispersed. Microcapsules are composed of a nucleus of active material coated with a layer of polymer.

Document EP-A-542,314 relates to a method for preparing particles of active material without coating with polymer by precipitation by virtue of an anti-solvent fluid in the supercritical state.

The object of the present invention is therefore firstly to provide a novel method involving a supercritical fluid which makes it possible to obtain microcapsules for which the coating agent is a polymer with a substantially polar nature.

Another object of the present invention is to provide novel microcapsules which are distinguished in particular from those which have been described above by their physical characteristics and by the absence of residual solvent in the coating layer.

The invention therefore firstly relates to a method for preparing microcapsules comprising an active substance coated with a layer of polar polymer, characterized in that it comprises the following stages:

suspending an active substance in a solution of substantially polar polymer in an organic solvent, the active substance being insoluble in this solvent, the said substantially polar polymer being insoluble in liquid $CO_2$ or $CO_2$ in the supercritical state, the said organic solvent being soluble in liquid $CO_2$ or supercritical $CO_2$, bringing the suspension into contact with liquid $CO_2$ or supercritical $CO_2$, so as to desolvate in a controlled way the substantially polar polymer and to provide coacervation of the polymer, substantially extracting the solvent by means of $CO_2$ in the supercritical state and discharging the $CO_2$/solvent mixture, if necessary by several cycles of introduction of $CO_2$, followed by pumping, recovering the microcapsules in the autoclave in dry powder form.

The expression "in a controlled way" is understood stood to mean the fact that the system is always under conditions close to equilibrium and is not subject to sudden variations in pressure (pressure reduction).

It will be noticed that this method differs radically from the method disclosed in European Patent Application No. 706,821, insofar as the polymer is at no point in solution in the fluid in the liquid or supercritical state.

Furthermore, this method is significantly simpler in comparison with conventional methods (emulsion-evaporation of the solvent), due to the elimination of the drying step, which is generally lengthy and difficult (10 to 15 days under 10 Pa dynamic vacuum).

The Supercritical Fluid

Although the subject-matter of the invention is more particularly a method involving $CO_2$ as fluid, the method can be extended to other fluids which are known to behave in a similar way to $CO_2$, such as those mentioned by J. P. Benoit et al. (op. cit.). Nevertheless, this method will be more particularly described in the case of $CO_2$.

The Coating Agent

The polymers with a substantially polar nature relating to the invention will be more particularly chosen from:

1) polysaccharides and their derivatives, such as:

starch or modified starch, such as carboxymethylstarches, or polysaccharides resulting from the depolymerization, by physical, chemical or enzymatic methods, of starch or its derivatives, cellulose or modified cellulose, such as carboxymethylcelluloses, ethylceluose, hydroxymethylcellulose, hydroxyethylcellulose, hydroxypropylcellulose, methylhydroxyethylcellulose or methylhydroxypropylcellulose, or polysaccharides resulting from the depolymerization, by a physical, chemical or enzymatic method, of cellulose or its derivatives, alginates extracted from brown algae, carrageenans of lambda, iota or kappa type extracted from red algae, pectins extracted from lemons, apples or beetroot, pectates which result from the demethylation of pectins, guars or modified guars, such as carboxymethylguars, xanthans, chitosans, 2) Synthetic polymers of the acrylic or methacrylic type, such as homopolymers or copolymers of acrylic or methacrylic acid or of esters of acrylic or methacrylic acid, polyacrylamide, polycyanoacrylates and generally all well known synthetic polymers derived from acrylic or methacrylic acid, vinyl polymers and copolymers derived from vinyl esters (poly(vinyl acetate)), or copolymers of ethylene and of vinyl acetate.

These polymers are insoluble in the fluid in liquid or supercritical state, in particular $CO_2$.

Mention will very particularly be made of the polymers of the type of those sold under the tradename Eudragit® by the company Röhm, such as the neutral acrylic or methacrylic ester copolymers resulting from the dehydration of aqueous dispersions (Eudragit® NE 30D and NE 40D), the copolymers of acrylic or methacrylic esters carrying quaternary ammonium groups (Eudragit® RL 100 and RS 100), the copolymers of acrylic or methacrylic esters carrying amine functional groups (Eudragit® E 100) or, finally, the copolymers of acrylic or methacrylic esters carrying carboxyl groups (Eudragit® L 100 and S 100).

3) Biodegradable polymers and copolymers of α-hydroxycarboxylic acids, in particular the homopolymers and copolymers of lactic and glycolic acids, 4) Poly(ε-caprolactone) and its derivatives, poly(β-hydroxybutyrate, poly(hydroxyvalerate) and (β-hydroxybutyrate-hydroxyvalerate) copolymers, or poly (malic acid).

5) Amphiphilic block polymers of poly(lactic acid)-poly (ethylene oxide) type.

6) Polycondensates, such as polyamides and polyesters (poly(ethylene terephthalate)), and polymers resulting from polyaddition (polydimethylsiloxane).

7) Polyanhydrides, polyorthoesters and polyphosphazenes.

These polymers, chosen in order to be efficient coating agents, exhibit a molar mass of greater than $10^3$ g/mol, preferably of greater than $2\times10^3$ g/mol and more particularly of between $2\times10^3$ and $2\times10^5$ g/mol.

The Active Substance

The active substance must be insoluble in the organic solvent. Mention may be made, without implied limitation, among the numerous substances which can be coated, of:

* Pharmaceutical products:

analgesics (in particular paracetamol)

antipyretics aspirin and derivatives antibiotics anti-inflammatories antiulceratives antihypertensives neuroleptics antidepressants oligonucleotides peptides proteins

* Cosmetic products:

self-tanning, anti-UV

* Processed foodstuffs:

vitamins

These active substances are provided in the form of a powder with a small particle size, typically of the order of a few micrometres and more generally from approximately 0.1 µm to approximately 800 µm.

A notable characteristic of the method according to the invention is that it can be carried out starting from particles of active materials of highly varied geometry, comprising both highly regular shapes or, in contrast, highly irregular shapes. The method can be used to encapsulate perfectly spherical particles, crystals or microcrystals which are non-spherical but which exhibit highly regular shapes, or particles of highly irregular shape. This can be, for example, powders obtained by crystallization, precipitation, pyrolysis, evaporation of a solution or atomization-drying but also powders resulting from a milling, a granulation, an extrusion method or any mechanical size reduction method. Porous solid particles can also be encapsulated by the said method. In this case, one of the characteristics of the coating lies in its ability to faithfully match the surface of the particles even into the pores and the cracks in the surface, because the desolation of the polymer and its precipitation or condensation at the surface of the particles is well controlled by the amount and the conditions of introduction (pressure, temperature) of the $CO_2$, the final microcapsule is then characterized by the absence of surface pores capable of exposing the active material to the external environment.

The Solvent for the Polymer

The choice of the solvent or mixture of solvents suitable in the context of the method according to the invention depends on the nature of the polymer to be dissolved.

In the case of acrylic polymers, mention will be made of ketones (cyclohexanones), alcohols (methanol, ethanol, butanol, isopropanol, propylene glycol), water/alcohol or acetone/alcohol mixtures, P.G.A. (poly(propylene glycol) acetate) or esters (ethyl acetate).

The solvent generally exhibits a polar protic or aprotic nature and is not an agent which entrains the polymer into the $CO_2$, i.e. it does not significantly increase the solubility of the polymer in supercritical $CO_2$.

Principle of the Method

In practice, the method is preferably carried out with stirring in a closed reactor, in particular an autoclave. The $CO_2$ is brought into contact in a controlled way with the suspension of active principle comprising the polymer in solution, either by introduction of the $CO_2$ into a closed reactor, in particular an autoclave already comprising the suspension, or by injection of the suspension into an autoclave comprising the $CO_2$.

It will be recalled that this intimate contact between the $CO_2$ and the suspension is provided either with a $CO_2$ in liquid/gas form (the liquid being mixed with the suspension and wetting the particles of active substance) or directly by $CO_2$ in the supercritical state.

According to one alternative form, the suspension is brought into contact with liquid $CO_2$ and then the pressure and/or the temperature is/are increased, so as to bring the $CO_2$ to the supercritical state, in order to extract the solvent.

The temperature of the liquid $CO_2$ is preferably between 20 and 50° C. and the pressure is preferably between 50 and $150 \times 10^5$ Pa. The temperature of the supercritical $CO_2$ is preferably between 35 and 45° C. and the pressure is preferably between 100 and $140 \times 10^5$ Pa.

The weight of solvent for the polymer introduced into the closed reactor, in particular the autoclave, represents at least 3% of the weight of supercritical fluid or liquid fluid used to bring about the desolation of the polymer and preferably between 3.5% and 25% of the weight of the fluid.

A phase separation takes place with coacervation (precipitation) of the polymer around the particles of active substance and passage of the solvent into the $CO_2$ phase.

The invention also relates to novel micro-capsules comprising an active substance coated in a layer of substantially polar polymer, characterized in that the polymer layer exhibits a low surface energy and in that the microcapsules can be obtained by the method according to the invention.

According to additional characteristics, the polymer layer matches the surface of the active substance particle even into the internal porosities and the microcapsules exhibit a surface devoid of pores exposing the active substance particle to the external environment.

These microcapsules are in fact novel per se for the following two reasons. This is because, firstly, the coating layer exhibits a conformation which is different on several accounts. It is characterized by the absence of surface pores which can expose the active material to the external environment and by the substantial absence of polar units at the surface of the microcapsule. For this reason, these microcapsules differ from those obtained by the conventional coacervation method as described above in the description. The origin of this different conformation is related to the fact that the desolation is carried out in a controlled way by virtue of the introduction of an appropriate amount of $CO_2$ under well-chosen pressure and temperature conditions and that the $CO_2$ exhibits an only slightly polar nature, which induces the orientation towards the surface of the particles of the least polar groups of the polymer.

Another notable aspect of the microcapsules according to the invention is that the coating layer is virtually devoid of solvent. In any case, it comprises less than 500 ppm of solvent and preferably less than 300 ppm of solvent.

Furthermore, because of their low surface energy, these novel microcapsules exhibit a greater barrier effect which, for this reason, slows down the deterioration in the coating layer and the diffusion of the active substance towards polar environments, such as physiological fluids, aqueous formulations, and the like. The size of these microcapsules varies between 10 nm and 1 mm and preferably between 20 nm and 500 µm.

The level of active substance is advantageously between 25 and 95% (by weight) and preferably between 60% and 90% (by weight).

The invention also relates to the application of these microcapsules in the preparation of cosmetic or pharmaceutical products or processed foodstuffs.

The invention will now be described by the non-limiting examples below.

EXAMPLE 1

40 mg of a methacrylic acid, alkyl acrylate and alkyl methacrylate copolymer, sold by the company Rohm under the tradename Eudragit L 100®, are dissolved in 54 ml of absolute ethanol. 200 mg of bovine hemoglobin (BH), originating from the company Sigma, are suspended in the solution thus obtained and the suspension is placed in an autoclave with a capacity of 1.5 l.

In a first step, the pressure is raised to $80 \times 10^5$ Pa by introducing liquid $CO_2$ while remaining at a constant temperature of 25° C. The $CO_2$ is therefore maintained in the liquid state.

The liquid $CO_2$ is mixed with the suspension, making it possible to suitably wet the hemoglobin. The liquid $CO_2$ ensures the gradual precipitation of the polymer. The $CO_2$ is brought to the supercritical state by increasing the pressure to $125 \times 10^5$ Pa and by jointly raising the temperature to 40° C. (which corresponds to a $CO_2$ relative density of approximately 0.72 kg/dm³), which makes it possible to extract the ethanol. These conditions are maintained for 15 minutes. The $CO_2$/ethanol mixture is discharged into the separator by decompressing to $75 \times 10^5$ Pa (in order to remain in the supercritical phase), in which separator the ethanol is recovered and the $CO_2$ returns to a tank. 25 ml of ethanol are recovered. Several successive cycles of introducing liquid $CO_2$, of bringing to the supercritical state and of discharging the $CO_2$/ethanol mixture are repeated until the ethanol has been completely removed. Decompression is necessarily carried out via the gas phase, in order not to reconcentrate the polymer in the remaining ethanol.

After the decompression step, the operation can thus be repeated several times by reintroducing $CO_2$, in order to restore a pressure of $125 \times 10^5$ Pa and a temperature of 40° C.

The $CO_2$/solvent mixture can subsequently be depressurized and released to the external environment and then fresh $CO_2$ can be introduced, which is brought to the supercritical state, in order to completely extract the solvent. The temperature in this case is generally between 35 and 45° C. and the pressure is between 100 and $140 \times 10^5$ Pa.

According to one alternative form, the suspension can also be directly brought into contact with supercritical $CO_2$ under the conditions shown above.

230 mg of microcapsules with a mean size of 200 to 300 μm and comprising 83.3% by weight of hemoglobin are recovered and no ethanol remains in the autoclave. The microcapsules are resistant to water. In fact, it is clearly seen, by virtue of microscopic observation, that the coated hemoglobin is not dissolved in a drop of water, whereas an uncoated sample rapidly gives a red coloring to the drop of water.

EXAMPLES 2–8

Several other tests carried out under the same conditions but in which the amount of bovine hemoglobin (BH) and the amount of solvent are varied gave the following results:

| Ex. | eth (ml) | BH (mg) | BH/Eudr (mg) | BH/Eudr |
|---|---|---|---|---|
| 2 | 50 | 500 | 500/99.9 | 83.31/16.7 |
| 3 | 50 | 515 | 515/50.31 | 91.1/8.9 |
| 4 | 50 | 511.5 | 511.5/158 | 76.4/23.6 |
| 5 | 50 | 1012.5 | 1012.5/103 | 90.8/9.2 |
| 6 | 50 | 233.4 | 233.4/100 | 70/30 |
| 7 | 50 | 501 | 501/101 | 83.2/16.8 |
| 8 | 50 | 502 | 502/101 | 83.2/16.8 | eth: ethanol
BH: bovine hemoglobin
Eudr: Eudragit L100 ®

Verification of the Quality of the Coating

The kinetics of dissolution of the micro-encapsulated hemoglobin in a phosphate buffer of pH=7 for one hour at 37° C. are compared with respect to non-encapsulated hemoglobin (control sample C). Withdrawals are made over time from a receptacle equipped with a stirrer, to the shaft of which is attached a paper bag comprising the sample to be tested, and the concentration of the sample is evaluated by visible spectrophotometry (405 nm=$\lambda_{max}$ of hemoglobin). It should be noted that Eudragit L-100 does not absorb at this wavelength.

The kinetics of dissolution are compared with those obtained for untreated hemoglobin.

The results are shown in the table below after dissolution for one hour.

| Sample | Concentration of BH (g/l) |
|---|---|
| Control C (100% loading level) | 0.1763 |
| 2 | 0.0343 |
| 3 | 0.019 |
| 4 | 0.0414 |
| 5 | 0.0048 |
| 6 | 0.0009 |
| 7 | 0.0286 |
| 8 | 0.0323 |

A pronounced delay in the release, due to the coating, is therefore found.

These kinetic measurements are represented in the appended figure (concentration of hemoglobin/time). A delay in the dissolution is clearly observed.

EXAMPLE 9

4 g of L-lactic acid homopolymer (PLA) Résomer® L 206 (sold by Boehringer-Ingelheim) are dissolved in 130 ml of dichloromethane. 8 g of bovine serum albumin (BSA) powder (sold by the company Sigma) are suspended in the solution thus obtained.

The pressure is raised to $80 \times 10^5$ Pa by introducing liquid $CO_2$, the temperature being maintained at 25° C. The $CO_2$ is thus maintained the liquid state.

The liquid $CO_2$ is mixed with the suspension and brings about the gradual precipitation of the polymer. The $CO_2$ is brought to the supercritical state by increasing the pressure to $90 \times 10^5$ Pa and by jointly raising the temperature to 40° C., which makes it possible to extract the dichloromethane.

These conditions are maintained for 30 min. The $CO_2$/dichloromethane mixture is discharged to the separator, in which separator the dichloromethane is recovered and the recycled $CO_2$ returns to the tank. Several successive cycles of introducing $CO_2$, of bringing to the supercritical state and of discharging the $CO_2$/dichloromethane mixture are repeated until the dichloromethane has been completely removed.

11.2 g of microcapsules are recovered in the autoclave in the form of a dry powder with a mean size of approximately 50 μm. Quantitative determination of the dichloromethane by gas chromatography, carried out after basic hydrolysis (1N NaOH) in the presence of isopropyl chloride as internal standard, shows that the level of residual dichloromethane in the microcapsules is less than or equal to 300 ppm (with respect to the polymer).

The level of BSA present in these capsules is determined by redissolving the microcapsules obtained in dichloromethane: this level is found of 68% (by weight, with respect to the total weight of micro-capsules).

What is claimed is:
1. A method for preparing microcapsules comprising an active substance coated with a layer of substantially polar polymer, comprising:
   suspending the active substance in a solution of substantially polar polymer in an organic solvent, the active substance being insoluble in the organic solvent, the substantially polar polymer being insoluble in liquid $CO_2$ or $CO_2$ in the supercritical state, the organic solvent being soluble in liquid $CO_2$ or supercritical $CO_2$, bringing the suspension into contact with liquid $CO_2$ so as to desolvate in a controlled way the substantially polar polymer and to provide its coacervation, wherein the suspension is brought into contact with the liquid $CO_2$ and then the pressure or the temperature or both is increased, so as to bring the $CO_2$ to the supercritical state, in order to extract the solvent, substantially extracting the solvent by means of the $CO_2$ in the supercritical state and discharging the $CO_2$/solvent mixture, and recovering the microcapsules.

2. The method of claim 1, wherein the polymer is selected from the group consisting of a polysaccharide, a cellulose derivative, a polymer derived from acrylic or methacrylic acid, a biodegradable polymer of poly($\alpha$-hydroxy acid), a polymer derived from a vinyl ester, a polyester, a polyamide, a polyanhydride, a polyorthoester, a polycyanoacrylate, and a polyphosphazene.

3. The method of claim 2, wherein the polymer has a molar mass of between $2\times10^3$ and $2\times10^5$ g/mol.

4. The method of claim 1, wherein the solvent is selected from the group consisting of a ketone, an alcohol, and an ester.

5. The method of claim 1, wherein the temperature of the liquid $CO_2$ is between 20 and 50° and the pressure is between 50 and $150\times10^5$ Pa.

6. The method of claim 1, wherein the temperature of the supercritical $CO_2$ is between 35 and 45° C. and the pressure is between 100 and $140\times10^5$ Pa.

7. The method of claim 1, wherein the supercritical $CO_2$/solvent mixture is discharged via the gas phase.

8. The method of claim 1, wherein the weight of solvent for the polymer represents at least 3% of the weight of supercritical fluid or liquid fluid used to bring about the desolvation of the polymer.

9. The method of claim 1, wherein the active substance has a particle size of between 10 nm and 1 mm.

10. The method of claim 9, wherein the active substance is selected from the group consisting of an analgesic, an antiulcerative, an antihypertensive, a neuroleptic, an antidepressant, an oligonucleotide, an antipyretic, aspirin and its derivatives, an anti-inflammatory, an antibiotic, a peptide and a vitamin.

11. The method of claim 1, wherein the method is carried out in a closed reactor.

12. A microcapsule comprising an active substance coated in a layer of substantially polar polymer selected from the group consisting of a polysaccharide, a cellulose derivative, a polymer derived from acrylic or methacrylic acid, a polycyanoacrylate, a biodegradable polymer of poly($\alpha$-hydroxy acid), a polymer derived from a vinyl ester, a polyester, a polyamide, a polyanhydride, a polyorthoester and a polyphosphazene, wherein the polymer layer has a low surface energy, the microcapsules being obtained by the method according to claim 1.

13. The microcapsule of claim 12, wherein the level of active substance by weight per microcapsule is between 25 and 95%.

14. The microcapsule of claim 12, wherein the mean diameter is between 10 nm and 1 mm.

15. The microcapsule of claim 12, wherein the polar polymer layer comprises less than 500 ppm of solvent.

16. The microcapsule of claim 12 in combination with a cosmetic or pharmaceutical product or processed foodstuff.

17. The method of claim 8, wherein the weight of solvent is 3.5 to 25% of the weight of the fluid.

18. The method of claim 9, wherein the particle size is between 20 nm and 50 $\mu$m.

19. The method of claim 10, wherein the analgesic is paracetamol.

20. The microcapsule of claim 13, wherein the level of active substance is 60 to 90%.

* * * * *

UNITED STATES PATENT AND TRADEMARK OFFICE
CERTIFICATE OF CORRECTION

PATENT NO. : 6,183,783 B1
DATED : February 6, 2001
INVENTOR(S) : Benoit et al.

It is certified that error appears in the above-identified patent and that said Letters Patent is hereby corrected as shown below:

Column 9,
Lines 8-9, delete "wherein the suspension is brought into contact with the liquid $CO_2$";
Line 12, delete "in order to extract the solvent,".

Signed and Sealed this

Nineteenth Day of August, 2003

JAMES E. ROGAN
*Director of the United States Patent and Trademark Office*